US007255863B2

(12) United States Patent
Dale

(10) Patent No.: US 7,255,863 B2
(45) Date of Patent: Aug. 14, 2007

(54) GROUP A STREPTOCOCCAL VACCINES

(75) Inventor: James B Dale, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 566 days.

(21) Appl. No.: 10/759,600

(22) Filed: Jan. 16, 2004

(65) Prior Publication Data

US 2005/0202037 A1    Sep. 15, 2005

Related U.S. Application Data

(62) Division of application No. 09/151,409, filed on Sep. 10, 1998, now Pat. No. 6,716,433.

(60) Provisional application No. 60/058,635, filed on Sep. 12, 1997.

(51) Int. Cl.
*A61K 39/00* (2006.01)
*A61K 39/09* (2006.01)
*A61K 39/02* (2006.01)
*A61K 38/00* (2006.01)
*C07K 1/00* (2006.01)
*C12N 15/09* (2006.01)

(52) U.S. Cl. .............................. 424/192.1; 424/244.1; 424/234.1; 424/184.1; 514/2; 530/300; 530/350; 530/825; 435/69.3

(58) Field of Classification Search ............. 424/244.1, 424/234.1, 192.1, 184.1; 514/2; 530/350, 530/300, 825; 435/69.3
See application file for complete search history.

(56) References Cited

U.S. PATENT DOCUMENTS

| 4,284,537 | A | 8/1981 | Beachey .................. 260/6 |
| 4,454,121 | A | 6/1984 | Beachey .................. 424/177 |
| 4,521,334 | A | 6/1985 | Beachey .............. 260/112.5 R |
| 4,597,967 | A | 7/1986 | Beachey .................. 424/88 |
| 4,705,684 | A | 11/1987 | Beachey .................. 424/88 |
| 4,784,948 | A | 11/1988 | Scott et al. .................. 435/68 |
| 4,919,930 | A | 4/1990 | Beachey et al. .............. 424/88 |
| 5,124,153 | A | 6/1992 | Beachey et al. .............. 424/93 |
| 5,334,379 | A | 8/1994 | Pillai et al. ................ 424/85.2 |
| 5,985,654 | A | 11/1999 | Fischetti et al. .......... 435/320.1 |
| 6,063,386 | A | 5/2000 | Dale et al. ................ 424/244.1 |
| 6,419,932 | B1 | 7/2002 | Dale ........................ 424/244.1 |

FOREIGN PATENT DOCUMENTS

| WO | WO 94/06421 | 3/1994 |
| WO | WO 94/06465 | 3/1994 |
| WO | WO 00/37648 | 6/2000 |

OTHER PUBLICATIONS

Ada, *Fundamental Immunology*, William E. Paul, M.D. (ed.), 2nd Edition, Raven Press, New York, 1989, pp. 1010-1011.

Baird et al., "Epitopes Of Group A Streptococcal M Protein Shared With Antigens Of Articular Cartilage And Synovim," *The Journal Of Immunology 149* (9):3132-3137, 1991.

Beachey and Ofek, "Epithelial Cell Binding Of Group A Streptococci By Lipoteichoic Acid On Fimbriae Denuded Of M Protein," *The Journal Of Experimental Medicine 143* :759-771, 1976.

Beachey and Seyer, "Protective And Nonprotective Epitopes Of Chemically Synthesized Peptides Of The $NH_2$-Terminal Region Of Type 6 Streptoccal M Protein," *The Journal Of Immunology 136* (6):2287-2292, 1986.

Beachey and Seyer, *Seminars in Infectious Disease. vol. IV Bacterial Vaccines*, Thieme-Stratton Inc., New York, New York, 1982, Chapter Fifty-Seven, "Primary Structure And Immuno-Chemistry Of Group A Streptoccal M Proteins," pp. 401-410.

Beachey and Stollerman, "Mediation of Cytotoxic Effects of Streptococcal M Protein by Nontype-Specific Antibody in Human Sera," *The Journal of Clinical Investigation 52*: 2563-2570, 1973.

Beachey and Stollerman, "Toxic Effects Of Steptococcal M Protein On Platelets And Polymorphonuclear Leukocytes In Human Blood," *The Journal Of Experimental Medicine 134*: 351-365, 1971.

Beachey et al., "Human Immune Response To Immunization With a Structurally Defined Polypeptide Fragment Of Streptococcal M Protein," *J. Exp. Med. 150*:862-877, 1979.

Beachey et al., "Immunogenicity In Animals And Man Of A Structurally Defined Polypeptide Of Streptococcal M Protein," *Transactions Of The Association Of American Physicians, vol. XCII*:pp. 346-354, 1979.

Beachey et al., "Opsonic Antibodies Evoked By Hybrid Peptide Copies Of Types 5 and 24 Streptococcal M Proteins Synthesized In Tandem," *J. Exp. Med. 163*: 1451-1458, 1986.

Beachey et al., "Peptic Digestion of Streptococcal M Protein. II. Extraction of M Antigen from Group A Streptococci With Pepsin," *Infection And Immunity 9*(5):891-896, 1974.

Beachey et al., "Primary Structure of Protective Antigens of Type 24 Streptococcal M Protein," *The Journal Of Biological Chemistry 255*(13):6284-6289, 1980.

Beachey et al., "Protective Immunogenicity And T Lymphocyte Specificity Of A Trivalent Hybrid Peptide Containing $NH_2$-Terminal Sequences Of Types 5, 6, And 24 M Proteins Synthesized In Tandem," *The Journal Of Experimental Medicine 166*:647-656, 1987.

(Continued)

*Primary Examiner*—S. Devi
(74) *Attorney, Agent, or Firm*—Seed IP Law Group PLLC

(57) ABSTRACT

The present invention provides methods for eliciting an immune response against Group A *streptococci*, comprising use of recombinant fusion polypeptides, and compositions thereof, that include a multivalent immunogenic portion of at least two immunogenic polypeptides from Group A *streptococci* M proteins (which are capable of stimulating a protective immune response against Group A *streptococci*), and a reiterated polypeptide from the immunogenic portion carboxy-terminal to the immunogenic portion, wherein the carboxy-terminal polypeptide is not required to stimulate an immune response against Group A *streptococci*.

26 Claims, 9 Drawing Sheets

OTHER PUBLICATIONS

Figure 1:
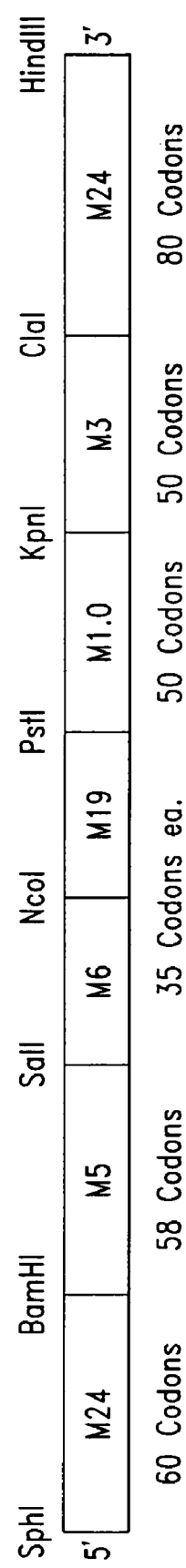

Beachey et al., "Purification And Properties Of M Protein Extracted From Group A Streptococci With Pepsin: Covalent Structure Of The Amino Terminal Region Of Type 24 M Antigen," *The Journal Of Experimental Medicine* 145:1469-1483, 1977.

Beachey et al., "Repeating Covalent Structure and Protective Immunogenicity of Native and Synthetic Polypeptide Fragments of Type 24 Streptococcal M Protein," *The Journal Of Biological Chemistry* 258(21):13250-13257, 1983.

Beachey et al., "Repeating covalent structure of streptococcal M protein," *Proc. Natl. Acad. Sci. USA* 75 (7):3163-3167, 1978.

Beachey et al., "Separation Of The Type Specific M Protein From Toxic Cross Reactive Antigens Of Group A Streptococci," *Transactions Of The Association Of American Physicians. Ninetieth Session vol. XC*: pp. 390-400, 1977.

Beachey et al., "Type-specific protective immunity evoked by synthetic peptide of *Streptococcus pyogenes* M Protein," *Nature* (London) 292:457-459, 1981.

Beall et al., "Sequencing emm-Specific PCR Products for Routine and Accurate Typing of Group A Streptococci," *Journal of Clinical Microbiology* 34 (4):953-958, Apr. 1996.

Blenden et al., "Growth of *Listeria monocytogenes* in a Corn Silage Extract Medium," *American Journal Of Veterinary Research* 29 (11):2237-2242, 1968.

Bricas et al., "Structure Et Synthese De La Subunite Peptide De La Paroi De Trois Bacteries Gram-Postif," *Peptides. Proceedings of the Eight European Peptide Symposium Sep. 1966*, Noordwijk, Neth., North-Holland Publishing Company: Amsterdam, Neth. And Interscience Publishers Division, John Wiley and Sons, Inc., New York, 1967, 286-292 (+ *Biological Abstracts* 50(4):Abstract No. 20361, 1936).

Bronze et al., "Protective And Heart-Cross Reactive Epitopes Located Within The $NH_2$Terminus Of Type 19 Streptococcal M Protein," *The Journal Of Experimental Medicine* 167:1849-1859, 1988.

Chou and Fasman, "Prediction of Protein Confirmation," *Biochemistry* 13(2):222-245, 1974.

Cunningham and Beachey, "Peptic Digestion of Streptococcal M Protein. I. Effect of Digestion at Suboptimal pH upon the Biological and Immunochemical Properties of Purified M Protein Extracts," *Infection And Immunity* 9(2):244-248, 1974.

Cunningham et al., "Human And Murine Antibodies Cross-Reactive With Streptococcal M Protein And Myosin Recognize The Sequence Gln-Lys-Ser-Lys-Gln In M Protein," *The Journal Of Immunology* 143 (8):2677-2683, 1989.

Dale, "Group A Streptococcal Vaccines," *New Vaccines And New Vaccine Technology* 13 (1):227-243, 1999.

Dale, "Group A Streptococcal Vaccines," *Pediatric Annals* 27:301-308, 1998.

Dale, "Multivalent group A streptococcal vaccine designed to optimize the immunogenicity of six tandem M protein fragments," *Vaccine* 17:193-200, 1999.

Dale and Beachey, "Multiple, Heart-Cross-Reactive Epitopes Of Streptococcal M Proteins," *Journal OF Experimental Medicine* 161:113-122, Jan. 1985.

Dale and Beachey, "Epitopes Of Streptococcal M Proteins Shared With Cardiac Myosin," *The Journal Of Experimental Medicine* 162:583-591, 1985.

Dale and Beachey, "Localization Of Protective Epitopes Of The Amino Terminus Of Type 5 Streptococcal M Protein," *The Journal Of Experimental Medicine* 163:1191-1202, 1986.

Dale and Beachey, "Sequence Of Myosin-Crossreactive Epitopes Of Streptococcal M Protein," *Journal Of Experimental Medicine* 164:1785-1790, 1986.

Dale et al., "Heterogencity Of Type-Specific And Cross-Reactive Antigenic Determinants Within A Single M Protein Of Group A Streptococci," *The Journal Of Experimental Medicine* 151:1026-1038, 1980.

Dale et al., "Blastogenic Responses Of Human Lymphocytes To Structurally Defined Polypeptide Fragments Of Streptococcal M Protein," *The Journal Of Immunology* 126(4):1499-1505, 1981.

Dale et al., "Type-Specific Immunogenicity Of A Chemically Synthesized Peptide Fragment Of Type 5 Streptococcal M Protein," *The Journal Of Experimental Medicine* 158:1727-1732, 1983.

Dale et al., "Recombinant Tetravalent Group A Streptococcal M Protein Vaccine," *Journal of Immunology* 151(4):2188-2194, Aug. 15, 1993.

Dale et al., "Intranasal immunization with recombinant group A streptococcal M protein fragment fused to the B subunit of *Escherichia coli* labile toxin protects mice against systemic challenge infections," *Journal of Infectious Diseases* 171(4):1038-1041, Apr. 1995 (abstract).

Dale et al., "Hyaluronate Capsule and Surface M Protein in Resistance to Opsonization of Group A Streptococci," *Infection And Immunity* 64(5):1495-1501, 1996.

Dale et al., "New protective antigen of group A streptococci," *J. Clin. Invest.* 103(9):1261-1268, 1999.

Dale et al., "Recombinant, octavalent group A streptococcal M protein vaccine", *Vaccine* 14(10):944-948, Jul. 1996.

Dixit et al., "Covalent Structure of Collagen: Amino Acid Sequence of α1-CB6A of Chick Skin Collagen," *Biochemistry* 14(9):1933-1938, 1975.

Edman and Begg, "A Protein Sequentor," *European J. Biochem.* 1:80-91, 1967.

Fischetti et al., "Surface Proteins form Gram-Positive Cocci Share Unique Structural Features," in Orefici (ed.), *New Persepectives on Streptococci and Streptococcal Infections. Proceedings of the XI Lancefield International Symposium on Streptococci and Streptococcal Diseases*, Siena, Italy, Sep. 10-14, 1990, Gustav Fischer verlag, Stuttgart, Jena, New York, 1992, pp. 165-167.

Fischetti, "Streptococcal M Protein," *Scientific American* :pp. 58-65, 1991.

Fischetti et al., "Protection Against Streptococcal Pharyngeal Colonization with a Vaccina: M Protein Recombinant," *Science* 244:1487-1490, 1989.

Freimer and McCarty, "Rheumatic Fever," *Scientific American* 213(6):67-74, 1965.

Gibbons et al., "Studies of Individual Amino Acid Residues of the Decapeptide Tyrocidine A by Proton Double-Resonance Difference Spectroscopy in the Correlation Mode," *Biochemistry*14 (2):420-437, 1975.

Goldsberg et al., "Serological Demonstration of H-Y (Male) Antigen on Mouse Sperm," *Nature* 232:478-480, 1971.

Hollingshead et al., "Complete Nucleotide Sequence of Type 6 M Protein of the Group A *Streptococcus,*" *The Journal Of Biological Chemistry* 261(4):1677-1686, 1986.

Hopp and Woods, "Prediction of protein antigenic determinants from amino acid sequences," *Proc. Natl. Acad. Sci. USA* 78(6):3824-3828, 1981.

Hruby et al., "Assembly and analysis of a functional vaccinia virus 'amplicon' containing the C-repeat from the M protein of *Streptococcus pyogenes,*" *Procedures of the National Academy of Sciences USA* 88:3190-3194, Apr. 1991.

Jones et al., "Differential Effects Of Antibodies To Lyt-2 And L3 T4 On Cytolysis By Cloned, Ia-Restricted T Cells Expressing Both Proteins," *The Journal Of Immunology* 139(2):380-384, 1987.

Kang, "Studies on the Location of Intermolecular Cross-Links in Collagen. Isolation of a CNBr Peptide Containing δ-Hydroxylysinonorleucine," *Biochemistry* 11(10):1828-1835, 1972.

Kang and Gross, "Amino Acid Sequence of Cyanogen Bromide Peptides from the Amino-Terminal Region of Chick Skin Collagen," *Biochemistry* 9(4):796-804, 1970.

Kaplan et al., "Group A Streptococcal Serotypes Isolated from Patients and Sibling Contacts During the Resurgence of Rheumatic Fever in the United States in the Mid-1980s," *The Journal Of Infectious Diseases* 159 (1):101-103, 1989.

Koch et al., "Purification And Structural Analysis Of Streptolysin S (SLS)," *Federation Proceedings* 42(7): p. 1810, Abstract No. 309, 1983.

Kraus et al., "Identification Of An Epitope Of Type I Streptococcal M Protein That Is Shared With A 43-kDa Protein Of Human Myocardium And Renal Glomeruli," *The Journal Of Immunology* 145(12):4089-4093, 1990.

Kraus et al., "Sequence And Type-Specific Immunogenicity Of The Amino-Terminal Region Of Type 1 Streptococcal M Protein," *The Journal Of Immunology 139*(9):3084-3090, 1987.

Lancefield, "Persistence Of Type-Specific Antibodies In Man Following Infection With Group A Streptococci," *J. Exp. Med. 110*:271-292, 1959.

Larver et al., "Antigenic drift in type A influenza virus: Peptide mapping and antigenic analysis of A/PR/8/34 (HON1) variants selected with monoclonal antibodies," *Proc. Natl. Acad. Sci. USA 76*(3):1425-1429, 1979.

Lockey, "Urticaria of Unknown Origin," *Hospital Practice*: pp. 49-57, 1979.

Manjula and Fischetti, "Tropomyosin-Like Seven Residue Periodicity In Three Immunologically Distinct Streptococcal M Proteins And Its Implications For The Antiphagocytic Property Of The Molecule," *J. Exp. Med. 151*:695-708, 1980.

Marston and Hartley, "Solubilization of Protein Aggregates," in *Methods in Enzymology, Guide to Protein Purification*, ed. MP Deutscher, vol. 182, section 20, pp. 264-276, 1991.

Miller et al., "Antigenic Variation among Group A Streptococcal M Proteins," *The Journal Of Biological Chemistry 263*(12):5668-5673, 1988.

Miller et al., "Conservation of Protective and Nonprotective Epitopes in M Proteins of Group A Streptococci," *Infection And Immunity 56*(8):2198-2204, 1988.

Mori et al., "Persistent Elevation of ImmunoglobulinG Titer against the C Region of Recombinant Group A Streptococcal M Protein in Patients with Rheumatic Fever," *Pediatric Research 39*(2): 336-342, 1996.

Mouw et al., "Molecular Evolution of Streptococcal M Protein: Cloning and Nucleotide Sequence of the Type 24 M Protein Gene and Relation to Other Genes of *Streptococcus pyogenes*," *Journal Of Bacteriology 170*(2):676-684, 1988.

Phillips, Jr. et al., "Streptococcal M protein: α-Helical coiled-coli structure and arrangement on the cell surface," *Proc. Natl. Acad. Sci. USA 78*(8):4689-4693, 1981.

Podbielski et al., "Application of the polymerase chain reaction to study the M protein(-like) gene family in beta-hemolytic streptococci," *Med. Microbiol. Immunol. 180*:213-227, 1991.

Rijin et al., "Group A Streptococcal Antigens Cross-Reactive With Mycocardium," *The Journal of Experimental Medicine 146*:579-599, 1977.

Robbins et al., "*Streptococcus pyogenes* Type 12 M Protein Gene Regulation by Upstream Sequences," *Journal Of Bacteriology 169*(12):5633-5640, 1987.

Sargent et al., "Sequence Of Protective Epitopes Of Streptococcal M Proteins Shared With Cardiac Sarcolemmal Membranes," *The Journal Of Immunology 139*(4):1285-1290, 1987.

Seyer and Kang, "Covalent Structure of Collagen: Amino Acid Sequence of Cyanogen Bromide Peptides from the Amino-Terminal Segment of Type III Collagen of Human Liver," *Biochemistry 16*(6):1158-1164, 1977.

Seyer et al., "Primary Structural Similarities Between Types 5 And 24 M Proteins Of *Streptococcous pyogenes*," *Biochemical And Biophysical Research Communications 92*(2):546-553, 1980.

Smithies et al., "Quantitative Procedures for Use with the Edman-Begg Sequenator. Partial Sequences of Two Unusual Immunoglobulin Light Chains, Rzf and Sac," *Biochemistry 10*(26):4912-4921, 1971.

Vashishtha et al., Reactivity of Antisera to Peptides Corresponding to the C-repeat Region of Streptococcal M Protein with Mammalian Coiled-Coli Proteins, *Abstracts Of The 91st General Meeting of the Society for Microbiology 1991*:p. 129, Abstract No. E-66, 1991.

Vashishtha and Fischetti, "Surface-Exposed Conserved Region of the Streptococcal M Protein Induces Antibodies Cross-Reactive with Denatured Forms of Myosin," *Journal of Immunology 150*(10): 4693-4701, May 15, 1993.

Weigent et al., "Induction of Human Gamma Interferon by Structurally Defined Polypeptide Fragments of Group A Streptococcal M Protein," *Infection And Immunity 43*(1):122-126, 1984.

Wistedt et al., "Identification of a plasminogen-binding motif in PAM, a bacterial surface protein," *Molecular Microbiology 18*(3): 569-578, 1995.

Wittner and Fox, "Homologous and Heterologous Protection of Mice with Group A Streptococcal M Protein Vaccines," *Infection and Immunity 15*(1):104-108, Jan. 1977.

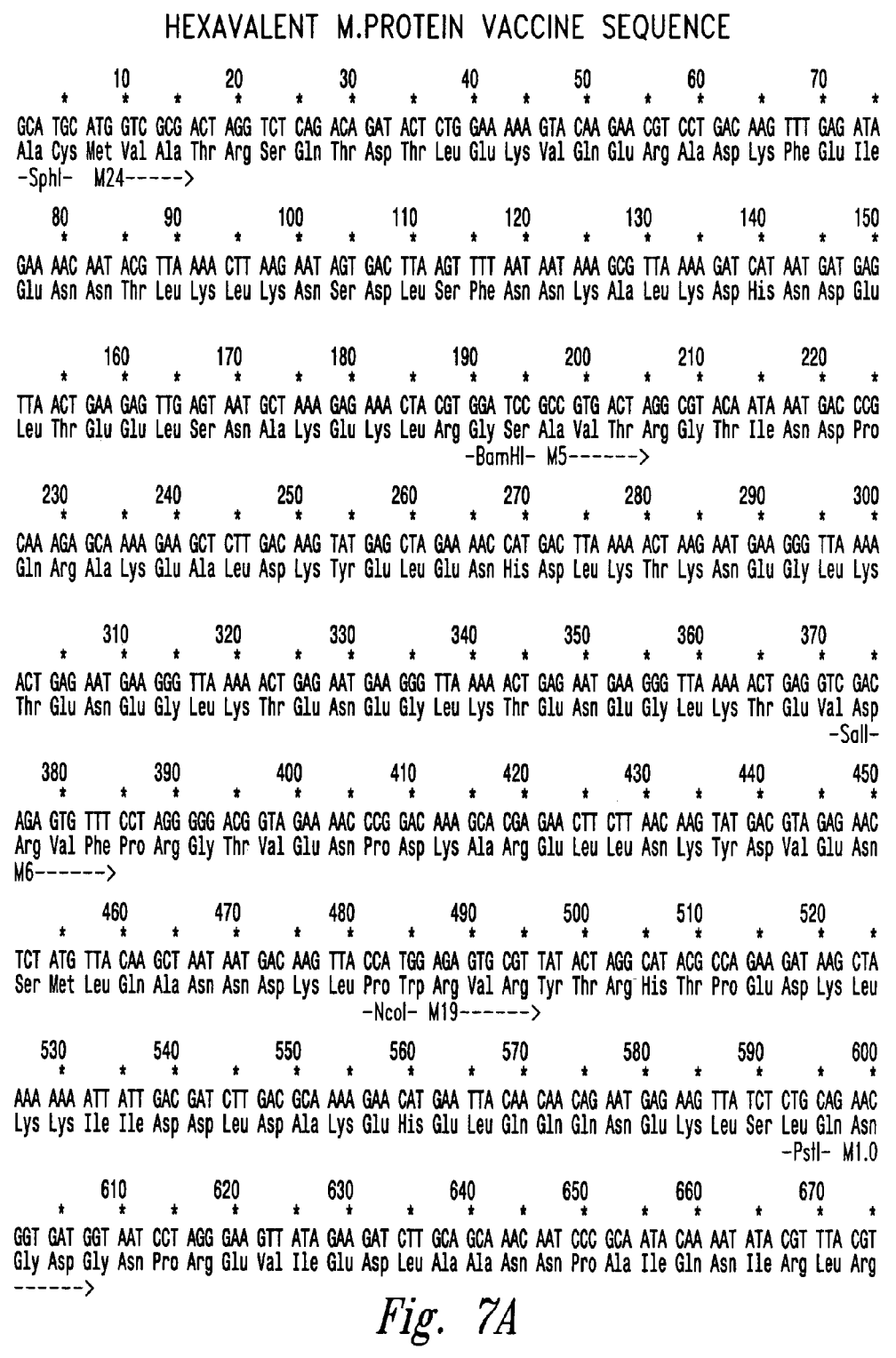

HEXAVALENT M.PROTEIN VACCINE SEQUENCE

```
        10          20          30          40          50          60          70
         *           *           *           *           *           *           *
GCA TGC ATG GTC GCG ACT AGG TCT CAG ACA GAT ACT CTG GAA AAA GTA CAA GAA CGT CCT GAC AAG TTT GAG ATA
Ala Cys Met Val Ala Thr Arg Ser Gln Thr Asp Thr Leu Glu Lys Val Gln Glu Arg Ala Asp Lys Phe Glu Ile
-SphI-  M24

```
      680         690         700         710         720         730         740         750
       *     *     *     *     *     *     *     *     *     *     *     *     *     *     *
CAC GAA AAC AAG GAC TTA AAA GCG AGA TTA GAG AAT GCA ATG GAA GTT GCA GGA AGA GAT TTT AAG AGA GCT GGT
His Glu Asn Lys Asp Leu Lys Ala Arg Leu Glu Asn Ala Met Glu Val Ala Gly Arg Asp Phe Lys Arg Ala Gly
                                                                                                KpnI 760         770         780         790         800         810         820
       *     *     *     *     *     *     *     *     *     *     *     *     *     *
ACC TTG TTA GAT CAG GTT ACA CAA TTA TAT ACT AAA CAT AAT AGT AAT TAC CAA CAA TAT AAT GCA CAA GCT GGC
Thr Leu Leu Asp Gln Val Thr Gln Leu Tyr Thr Lys His Asn Ser Asn Tyr Gln Gln Tyr Asn Ala Gln Ala Gly
--- M3----->

830         840         850         860         870         880         890         900
       *     *     *     *     *     *     *     *     *     *     *     *     *     *
AGA CTT GAC CTG AGA CAA AAG GCT GAA TAT CTA AAA GGC CTT AAT GAT TGG GCT GAG AGG CTG TTA CAA GAG TTA
Arg Leu Asp Leu Arg Gln Lys Ala Glu Tyr Leu Lys Gly Leu Asn Asp Trp Ala Glu Arg Leu Leu Gln Glu Leu 910         920         930         940         950         960         970
       *     *     *     *     *     *     *     *     *     *     *     *     *     *
AAT ATC GAT GTC GCG ACT AGG TCT CAG ACA GAT ACT CTG GAA AAA GTA CAA GAA CGT GCT GAC AAG TTT GAG ATA
Asn Ile Asp Val Ala Thr Arg Ser Gln Thr Asp Thr Leu Glu Lys Val Gln Glu Arg Ala Asp Lys Phe Glu Ile
      -ClaI- M24----->
     980         990        1000        1010        1020        1030        1040        1050
       *     *     *     *     *     *     *     *     *     *     *     *     *     *
GAA AAC AAT ACG TTA AAA CTT AAG AAT AGT GAC TTA AGT TTT AAT AAT AAA GCG TTA AAA GAT CAT AAT GAT GAG
Glu Asn Asn Thr Leu Lys Leu Lys Asn Ser Asp Leu Ser Phe Asn Asn Lys Ala Leu Lys Asp His Asn Asp Glu 1060        1070        1080        1090        1100        1110        1120
       *     *     *     *     *     *     *     *     *     *     *     *     *     *
TTA ACT GAA GAG TTG AGT AAT GCT AAA GAG AAA CTA CGT AAA AAT GAT AAA TCA CTA TCT GAA AAA GCT AGT AAA
Leu Thr Glu Glu Leu Ser Asn Ala Lys Glu Lys Leu Arg Lys Asn Asp Lys Ser Leu Ser Glu Lys Ala Ser Lys 1130        1140        1150
    *     *     *     *     *     *
ATT CAA GAA TTA GAG GCA CGT AAG TAA AAG CTT
Ile Gln Glu Leu Glu Ala Arg Lys *** Lys Leu
                                Stop HindIII
```

*Fig. 7B*

GROUP A STREPTOCOCCAL VACCINES

CROSS-REFERENCE TO RELATED APPLICATIONS

This application is a divisional of U.S. patent application Ser. No. 09/151,409, filed Sep. 10, 1998, now U.S. Pat. No. 6,716,433, which application claims the benefit of U.S. Provisional Application No. 60/058,635, filed Sep. 12, 1997, which applications are incorporated by reference in their entirety.

STATEMENT REGARDING FEDERALLY SPONSORED RESEARCH OR DEVELOPMENT

This invention was made with government support under Contract No. AI 10085-33 awarded by the National Institutes of Health and Grant No. 614-001 awarded by the Veteran's Administration. The government may have certain rights in this invention.

TECHNICAL FIELD

The present invention provides pharmaceutical compositions and methods, and in particular, vaccines for use in preventing Group A streptococcal infections.

BACKGROUND OF THE INVENTION

*Streptococci* are a group of bacteria with the capacity to grow in chains. Many varieties are part of the normal bacterial flora in humans and are not especially harmful. However, a particular group of streptococcal bacteria, called group A and represented by *Streptococcus pyogenes*, is a human pathogen. Briefly, group A *streptococci* cause a variety of human illnesses, ranging from uncomplicated pharyngitis and pyoderma to life-threatening infections associated with toxic shock syndrome, deep tissue invasion and sepsis. In some individuals, untreated streptococcal pharyngitis may be followed by acute rheumatic fever. In recent years there has been a dramatic increase in the incidence of severe streptococcal infections (Davies et al., "Invasive group A streptococcal infections in Ontario, Canada. Ontario group A Streptococcal study group," *N. Engl. J. Med.* 335: 547-554, 1996) and in the incidence of rheumatic fever (Veasey et al., "Resurgence of acute rheumatic fever in the intermountain region of the United States," *N. Eng. J. Med.* 316: 421-427, 1987).

Although streptococcal infections can be generally treated with antibiotics, in at least 4% of cases the infection leads to acute rheumatic fever. This disease is particularly prevalent in developing countries such as India, where millions of school-age children are affected.

The present invention provides new Group A streptococcal vaccines with enhanced immunogenicity, and further, provides other related advantages.

SUMMARY OF THE INVENTION

Briefly stated, the present invention provides immunogenic synthetic fusion polypeptides which stimulate an immune response against Group A *streptococci*. Within one aspect such polypeptides comprise (a) at least two immunogenic polypeptides from a Group A *streptococci* of at least 10 amino acids in length which are capable of stimulating an immune response against Group A *streptococci*, and a peptide C terminal to the immunogenic polypeptide which protects the immunogenicity of the immunogenic portion. Within preferred embodiments, the C-terminal peptide is not required to stimulate an immune response against Group A *streptococci* and hence, may be an inconsequential non-immunogenic peptide, or a reiterated immunogenic polypeptide. Within certain embodiments, the immunogenic polypeptide can be obtained from a wide variety of Group A *streptococci* (ranging from "1" to greater than "90"), including for example, Types 1, 1.1, 2, 3, 4, 5, 6, 11, 12, 13, 14, 18, 19, 22, 24, 28, 30, 48, 49, 52, 55 and 56.

Within other aspects of the present invention, vaccinating agents are provided for promoting an immune response against Group A *streptococci*, comprising (a) at least two immunogenic polypeptides from a Group A *streptococci* of at least 10 amino acids in length which are capable of stimulating a protective immune response against Group A *streptococci*, and (b) a peptide C terminal to the immunogenic polypeptide which protects the immunogenicity of the immunogenic portion, wherein the C-terminal peptide is not required to stimulate an immune response against Group A *streptococci*. As above, the polypeptide may be selected from a wide variety of Group A *streptococci* (ranging from "1" to greater than "90"), including for example, types 1.1, 2, 3, 4, 5, 6, 11, 12, 13, 14, 18, 19, 22, 24, 28, 30, 48, 49, 52, 55 and 56. Within certain further embodiments, the vaccinating agent may further comprise an adjuvant, such as, for example, alum, Freund's adjuvant, and/or an immunomodulatory cofactor (e.g., IL-4, IL-10, γ-IFN, or IL-2, IL-12 or IL-15).

Also provided are methods for vaccinating a host against Group A *streptococci* infections, comprising administering a vaccinating agent as described above.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIG. 1 is a schematic of the hexavalent vaccine indicating the length of each emm gene fragment and the restriction sites that were synthesized into the original PCR primers. Each of the emm gene fragments starts at the first codon that encodes the mature native protein except the emm3 fragment, which represents codons 21-70.

FIG. 2 is a SDS-polyacrylamide gel electrophoresis of the purified hexavalent protein stained with Coomassie™ blue. Computer-assisted image analysis of the stained protein bands indicated that the hexavalent protein (M.W. 45 kDa) accounted for 86% to 89% of the total protein in each sample.

FIGS. 3A and 3B are ELISA's of antisera from three rabbits immunized with the hexavalent vaccine in either alum or CFA. Titers are expressed as the inverse of the last dilution of serum that resulted in an O.D of >0.1. The ELISA antigen was the purified hexavalent protein. Each symbol represents serum from one rabbit.

FIGS. 4A-4F are ELISA's of antisera from rabbits immunized with the hexavalent protein in alum. Titers were determined using the purified pepsin-extracted M proteins (pep M) from the respective serotypes of group A *streptococci*. Each symbol represents one of three immunized rabbits.

FIG. 5 depicts in vitro opsonization assays of antisera from rabbits immunized with the hexavalent protein in alum.

Rotation mixtures consisted of the test organism, 0.1 ml of immune serum, and 0.4 ml of nonimmune human blood. The mixture was rotated for 45 minutes and the percentage of PMNs that had ingested or were associated with *streptococci* was estimated by microscopic counts of stained smears. In each assay, the preimmune serum resulted in <10% percent opsonization. Each different bar represents serum from one of the three immunized rabbits.

Figure 6:
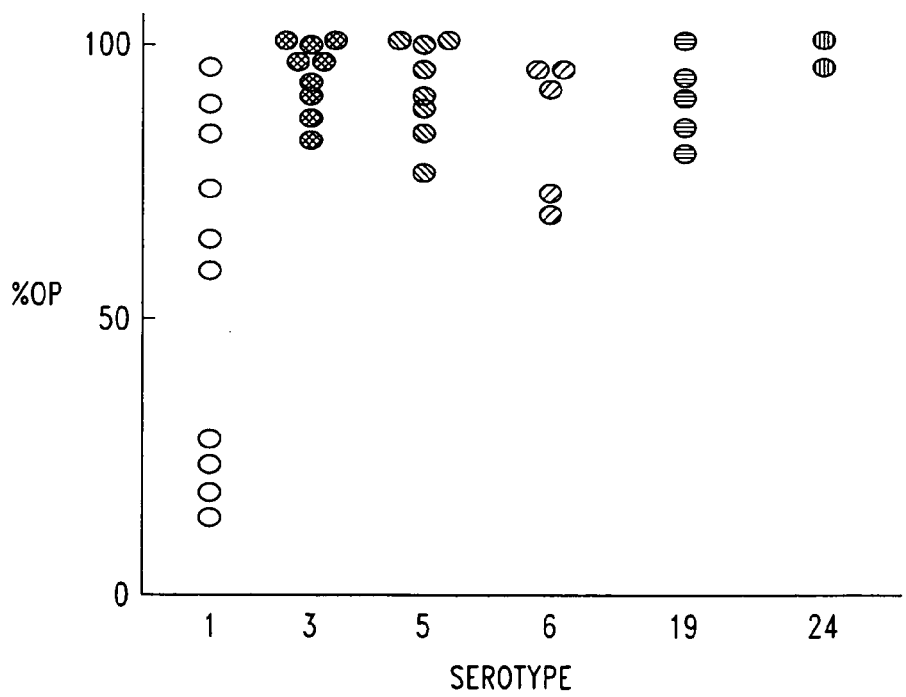

FIG. 6 is a graph which depicts opsonization of different strains within the same serotype of group A *streptococci* promoted by hexavalent rabbit antisera. Each symbol represents a strain of group A *streptococci* of the serotype indicated on the horizontal axis. Opsonization assays were performed as described below in the Examples.

FIGS. 7A and 7B show a nucleic acid sequence (SEQ ID NO:15) and predicted amino acid sequence (SEQ ID NO:16) of a hexavalent M protein vaccine.

DETAILED DESCRIPTION OF THE INVENTION

Definitions

Prior to setting forth the invention, it may be helpful to an understanding thereof to first set forth definitions of certain terms that will be used hereinafter.

"Vaccinating Agent" refers to a composition which is capable of stimulating a protective immune response within the host which receives the vaccinating agent. The vaccinating agent may be either protein, or, DNA-based (e.g., a gene delivery vehicle). Within further aspects, a prokaryotic host may be generated to be a vaccinating agent, and designed to express an immunogenic polypeptide or multivalent construct of the present invention (see, e.g., U.S. application Ser. No. 07/540,586).

"Gene delivery vehicle" refers to a recombinant vehicle, such as a recombinant viral vector, a nucleic acid vector (such as plasmid), a naked nucleic acid molecule such as genes, a nucleic acid molecule complexed to a polycationic molecule capable of neutralizing the negative charge on the nucleic acid molecule and condensing the nucleic acid molecule into a compact molecule, a nucleic acid associated with a liposome (Wang et al., *PNAS* 84: 7851, 1987), a bacterium, and certain eukaryotic cells such as a producer cell, that are capable of delivering a nucleic acid molecule having one or more desirable properties to host cells in an organism.

As noted above, the present invention provides vaccinating agents suitable for preventing Group A streptococcal infections. Briefly, as described in more detail below it has been discovered that, in order to optimize the immunogenicity of all aspects of a multivalent vaccine. Within one aspect of the invention, immunogenic synthetic fusion polypeptides which stimulate an immune response against Group A *streptococci* are provided. Such polypeptides generally comprise (a) at least two immunogenic polypeptides from a Group A *streptococci* of at least 10 amino acids in length which are capable of stimulating an immune response against Group A *streptococci*, and (b) a peptide C terminal to the immunogenic polypeptide which protects the immunogenicity of the immunogenic portion, wherein the C-terminal peptide is not required to stimulate an immune response against Group A *streptococci*. Particularly preferred protective peptides are generally at least ten amino acids in length, and may be 30 amino acids or longer.

Identification of Immunogenic Polypeptides, for Use in Vaccinating Agents

Immunogenic polypeptides suitable for use within the present invention may be readily identified and generated given the disclosure of the subject application (see also Dale and Beachey, *J. Exp. Med.* 163: 1191-1202; 1986; Beachey et al., *Nature* 292: 457-459, 1981; Dale et al., *J. Immunol.* 151: 2188-2194; 1993; and U.S. Pat. Nos. 4,454,121; 4,521,334; 4,597,967; 4,705,684; 4,919,930; and 5,124,153). Particularly preferred polypeptides can be obtained within the 50 amino acid residues of the N-terminus of an M protein.

Serotypes of Group A *streptococci* can be readily obtained from clinical isolates, from university collections (e.g., Rockefeller University Collection, 1230 York Avenue, New York, N.Y.) or from depositories such as the American Type Culture Collection (10801 University Boulevard, Manassas, Va.). Furthermore, sequences for Group A *streptococci* serotypes are available from the Centers for Disease Control, Atlanta, Ga.

A. Identification of Opsonic Epitopes of M Proteins

To demonstrate directly that opsonic M protein epitopes could be separated from autoimmune epitopes, peptides are copied from various serotypes (e.g., the amino-terminal 20-50 amino acids of M5 (Beachey et al., "Purification and properties of M protein extracted from group A *streptococci* with pepsin: Covalent structure of the amino terminal region of the type 24 M antigen," *J. Exp. Med.* 145: 1469-1483, 1977). SM5(1-20) failed to react with affinity purified pep M5 heart-reactive antibodies (Beachey et al., "Purification and properties of M protein extracted from group A *streptococci* with pepsin: Covalent structure of the amino terminal region of the type 24 M antigen," *J. Exp. Med* 145: 1469-1483, 1977). Rabbits immunized with SM5(1-20) coupled to tetanus toxoid developed high titers of antibodies against pep M5 that opsonized type 5 *streptococci* (Beachey et al., "Purification and properties of M protein extracted from group A *streptococci* with pepsin: Covalent structure of the amino terminal region of the type 24 M antigen," *J. Exp. Med.* 145: 1469-1483, 1977). Most importantly, none of the immune sera crossreacted with human myocardium.

B. Tissue-Crossreactive Epitopes of M Proteins

M proteins evoke antibodies that crossreact with a variety of human tissues and antigens within those tissues (Baird et al., "Epitopes of group A streptococcal M protein shared with antigens of articular cartilage and synovium," *J. Immunol.* 146: 3132-3137, 1991; Bronze, M. S and Dale, J. B., "Epitopes of streptococcal M proteins that evoke antibodies that cross-react with human brain," *J. Immunol.* 151: 2820-2828., 1993; Dale, J. B and Beachey E. H., "Protective antigenic determinant of streptococcal M protein shared with sarcolemmal membrane protein of human heart," *J. Exp. Med* 156: 1165-1176, 1982). In order to determine cross-reactivity, a series of overlapping peptides is synthesized that copies a selected fragment (e.g., M5), and used to either inhibit or evoke tissue-crossreactive antibodies. For example, the myosin-crossreactive antibodies evoked by pep M5 in rabbits were almost totally inhibited by peptide 84-116 of pep M5. This peptide spans the region between the A and B repeats of M5 and includes the degenerate A6 repeat. Murine and human myosin-crossreactive antibodies reacted with an epitope in peptide 183-189, which is located in the region between the B and C repeats of the intact M5 molecule.

Additional sarcolemmal membrane crossreactive epitopes are localized to peptide 164-197. Several epitopes of M5 that evoked antibodies that crossreacted with articular cartilage and synovium can also be found within the B repeats and the region spanning the A and B repeats of M5. The brain-crossreactive epitopes of M6 that were shared with other M proteins are localized to the B repeat region of the molecule.

Many of the tissue-crossreactive epitopes are shared among types 5, 6, 18 and 19 M proteins (Bronze, M. S and Dale, J. B., "Epitopes of streptococcal M proteins that evoke antibodies that cross-react with human brain," *J. Immunol.* 151: 2820-2828., 1993). Primary structural data reveals that all of these M proteins contain similar sequences within their B repeats (Dale et al., "Recombinant tetravalent group A streptococcal M protein vaccine," *J. Immunol.* 151: 2188-2194, 1993; Dale et al., "Recombinant, octavalent group A streptococcal M protein vaccine," *Vaccine* 14: 944-948, 1996; Dale et al., "Type-specific immunogenicity of a chemically synthesized peptide fragment of type 5 streptococcal M protein," *J. Exp. Med.* 158: 1727-1732, 1983), which is most likely the location of the shared heart brain and joint-crossreactive epitopes.

It should be emphasized that it is not necessary to localize the tissue-specific epitope, but rather, to first localize protective epitopes and ensure that they are not tissue-reactive.

Once a suitable immunogenic polypeptide for a selected serotype has been identified, it may be, optionally, combined with immunogenic polypeptides from other serotypes, in order to construct a multivalent vaccine. In this regard, preferred vaccines include vaccines developed from a combination of serotypes such as 1, 1.1, 2, 3, 4, 5, 6, 11, 12, 13, 14, 18, 19, 22, 24, 28, 30, 48, 49, 52 and 56 (for serotype 30 see Nakashima et al., *Clinic Infec. Dis.* 25: 260, 1997). Representative examples include vaccine such as 24, 5, 6, 19, 1, 3, X; and 1, 3, 5, 6, 18, 19, 22, 24, 28, 30, and X, wherein X is the C-terminal protective polypeptide.

Preparation of Vaccinating Agents

Vaccinating agents of the present invention can be synthesized chemically (see, e.g., Beachey et al., *Nature* 292: 457-459, 1981), or generated recombinantly. For recombinant production, PCR primers can be synthesized to amplify desired 5' sequences of each emm gene, and each primer is extended to contain a unique restriction enzyme site used to ligate the individual PCR products in tandem.

As noted above, the C-terminal portion of the vaccinating agent is constructed so as to contain a selective portion that can be lost or cleaved in vivo without affecting the efficacy of the vaccine. This may be accomplished by, for example, including an inconsequential non-immunogenic polypeptide at the end, or, including an immunogenic polypeptide that does not adversely impact the efficiency of the vaccine (e.g., a reiterated immunogenic polypeptide may be included at the end of the vaccine). Furthermore, protective antigens from unrelated pathogens can also be combined into a single polypeptide, which may circumvent the need for carriers. Vaccines against some pathogens might include T and B cell epitopes originally derived from different proteins on the same hybrid construct. Additionally, multivalent hybrid proteins may be sufficient conjugates in carbohydrate vaccines, such as those for *S. pneumoniae, H influenza* B or group B *streptococci.*

For protein expression, the multivalent genes are ligated into any suitable replicating plasmid which is used to transform an appropriate prokaryote host strain. Prokaryotes include gram negative or gram positive organisms, for example *E. coli* or bacilli. Suitable prokaryotic hosts cells for transformation include, for example, *E. coli, Bacillus subtilis, Salmonella typhimurium*, and various other species within the genera *Pseudomonas, Streptomyces*, and *Staphylococcus.*

Expression vectors transfected into prokaryotic host cells generally comprise one or more phenotypic selectable markers such as, for example, a gene encoding proteins that confer antibiotic resistance or that supplies an auxotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017), Briefly, pBR322 contains genes for ampicillin and tetracycline resistance and thus provides simple means for identifying transformed cells. The pBR322 "backbone" sections are combined with an appropriate promoter and a mammalian ETF structural gene sequence. Other commercially available vectors include, for example, pKK223-3 (Pharmacia Fine Chemicals, Uppsala, Sweden), pQE30 (6× His-tag expression vector), and pGEM1 (Promega Biotec, Madison, Wis., USA).

Common promoter sequences for use within prokaryotic expression vectors include β-lactamase (penicillinase), lactose promoter system (Chang et al., *Nature* 275: 615, 1978; and Goeddel et al., *Nature* 281: 544, 1979), tryptophan (trp) promoter system (Goeddel et al., *Nucl. Acids Res.* 8: 4057, 1980; and EPA 36,776) and tac promoter (Sambrook et al., *Molecular Cloning: A Laboratory Manual*, Cold Spring Harbor Laboratory, (1989)). A particularly useful prokaryotic host cell expression system employs a phage $\lambda$ $P_L$ promoter and a c1857ts thermolabile repressor sequence. Plasmid vectors available from the American Type Culture Collection that incorporate derivatives of the $\lambda$ $P_L$ promoter include plasmid pHUB2 (resident in *E. coli* strain JMB9 (ATCC 37092)) and pPLc28 (resident in *E. coli* RR1 (ATCC 53082)).

Transformation of the host strains of *E. coli* is accomplished by electroporation using standard methods (Dale et al., "Recombinant tetravalent group A streptococcal M protein vaccine," *J. Immunol.* 151: 2188-2194, 1993; Dale et al., "Recombinant, octavalent group A streptococcal M protein vaccine," *Vaccine* 14: 944-948, 1996). Successful transformants are identified by colony blots using rabbit antisera raised against one of the native M proteins or a synthetic peptide copy of the amino-terminus of one of the M proteins included in the multivalent protein.

The molecular size and antigenicity of the recombinant protein expressed by selected clones are determined by performing Western blots of extracts of *E. coli* (Dale et al., "Recombinant tetravalent group A streptococcal M protein vaccine," *J. Immunol.* 151: 2188-2194, 1993) using rabbit antisera raised against each native M protein purified from pepsin extracts of live *streptococci* (Beachey et al., "Purification and properties of M protein extracted from group A *streptococci* with pepsin: Covalent structure of the amino terminal region of the type 24 M antigen," *J. Exp. Med.* 145: 1469-1483, 1977). The multivalent gene is sequenced by the dideoxy-nucleotide chain termination method to confirm that each gene fragment is an exact copy of the native emm sequence.

Gene-Delivery Vehicle-Based Vaccines

Injection of mammals with gene delivery vehicles (e.g., naked DNA) encoding antigens of various pathogens has been shown to result in protective immune responses (Ulmer et al., *Science* 259: 1745-9, 1993; Bourne et al., *J. Infect. Dis.* 173: 800-7, 1996; Hoffman et al., *Vaccine* 12: 1529-33, 1994). Since the original description of in vivo expression of foreign proteins from naked DNA injected into muscle tissue (Wolff et al., *Science* 247: 1465-8, 1990), there have been several advances in the design and delivery of DNA for purposes of vaccination.

The M protein vaccines described above are ideally suited for delivery via naked DNA because protective immunity is ultimately determined by antibodies. For example, within one embodiment the multivalent genes are ligated into plasmids that are specifically engineered for mammalian cell expression (see, e.g., Hartikka et al., *Hum Gene Ther* 7: 1205-17, 1996, which contains the promoter/enhancer element from cytomegalovirus early gene, the signal peptide from human tissue plasminogen activator and a terminator element from the bovine growth hormone gene). The M protein hybrid genes can be cloned into the plasmid which is used to transfect human cell lines to assure recombinant protein expression. The plasmid is propagated in *E. coli* and purified in quantities sufficient for immunization studies by cesium chloride gradient centrifugation. Mice are immunized with 50 ug of plasmid in 50 ul saline given intramuscularly into the rectus femoris. Booster injections of the same dose are given at three and six weeks after the initial injection.

A wide variety of other gene delivery vehicles can likewise be utilized within the context of the present invention, including for example, viruses, retrotransposons and cosmids. Representative examples include adenoviral vectors (e.g., WO 94/26914, WO 93/9191; Yei et al., *Gene Therapy* 1:192-200, 1994; Kolls et al., *PNAS* 91(1):215-219, 1994; Kass-Eisler et al., *PNAS* 90(24):11498-502, 1993; Guzman et al., *Circulation* 88(6):2838-48, 1993; Guzman et al., *Cir. Res.* 73(6):1202-1207, 1993; Zabner et al., *Cell* 75(2):207-216, 1993; Li et al., *Hum Gene Ther.* 4(4):403-409, 1993; Caillaud et al., *Eur. J. Neurosci.* 5(10):1287-1291, 1993), adeno-associated type 1 ("AAV-1") or adeno-associated type 2 ("AAV-2") vectors (see WO 95/13365; Flotte et al., *PNAS* 90(22):10613-10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218). Methods of using such vectors in gene therapy are well known in the art, see, for example, Larrick, J. W and Burck, K. L., *Gene Therapy: Application of Molecular Biology*, Elsevier Science Publishing Co., Inc., New York, N.Y., 1991; and Kreigler, M., *Gene Transfer and Expression: A Laboratory Manual*, W. H. Freeman and Company, New York, 1990.

Gene-delivery vehicles may be introduced into a host cell utilizing a vehicle, or by various physical methods. Representative examples of such methods include transformation using calcium phosphate precipitation (Dubensky et al., *PNAS* 81:7529-7533, 1984), direct microinjection of such nucleic acid molecules into intact target cells (Acsadi et al., *Nature* 352:815-818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413-7417, 1989), microprojectile bombardment (Williams et al., *PNAS* 88:2726-2730, 1991), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al, *J. of Biol. Chem.* 264:16985-16987, 1989), as well as psoralen inactivated viruses such as Sendai or Adenovirus.

Serum from mice immunized with gene delivery vehicles containing multivalent M protein genes are assayed for total antibody titer by ELISA using native M proteins as the antigen. Serum opsonic antibodies are assayed as described above. Protective efficacy of DNA M protein vaccines is determined by direct mouse protection tests using the serotypes of group A *streptococci* represented in the vaccine.

Formulation and Administration

For therapeutic use, vaccinating agents can be administered to a patient by a variety of routes, including for example, by intramuscular, subcutaneous, and mucosal routes. The vaccinating agent may be administered as a single dosage, or in multiple units over an extended period of time. Within preferred embodiments, the vaccinating agent is administered to a human at a concentration of 50-300 ug per single site intramuscular injection. Several injections can be given (e.g., three or four) at least one month apart in order to further increase vaccine efficacy.

Typically, the vaccinating agent will be administered in the form of a pharmaceutical composition comprising purified polypeptide in conjunction with physiologically acceptable carriers, excipients or diluents. Such carriers will be nontoxic to patients at the dosages and concentrations employed. Ordinarily, the preparation of such compositions entails combining the vaccinating agent with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

Within preferred embodiments of the invention, the vaccinating agent is combined with an adjuvant, such as, for example, Freund's adjuvant, alum and the like.

The following examples are offered by way of illustration, and not by way of limitation.

EXAMPLES

Example 1

Construction and Expression of a Hexavalent Fusion Gene

A hexavalent emm gene was constructed using PCR to amplify specific 5' regions of the six different emm genes (24, 5, 6, 19, 1 and 3) essentially as described previously (Dale et al., "Recombinant tetravalent group A streptococcal M protein vaccine," *J. Immunol.* 151:2188-2194, 1993; Dale et al., "Recombinant, octavalent group A streptococcal M protein vaccine," *Vaccine* 14:944-948, 1996).

Briefly, the multivalent genes are constructed using PCR and primers that specify specific 5' emm gene fragments.

The gene fragments may range in size from 30 bp to 300 bp. Chromosomal DNA from each serotype of group A *streptococcus* is used as the template for the PCR reactions. For the hexavalent emm gene described in the example, the PCR primers are as follows:

```
M24-1 TS
                                         (SEQ ID NO:1)
        SphI
5' GGG GGG GCA TCG GTC GCG ACT AGG TCT CAG ACA
GAT 3'

M24-1 BS
                                         (SEQ ID NO:2)
        BamH1
5' GGG GGG GGA TCC ACG TAG TTT CTC TTT AGC 3'

M5 TS
                                         (SEQ ID NO:3)
        BamH1
5' GGG GGG GGA TCC GCC GTG ACT AGG GGT ACA 3'

M5 BS
                                         (SEQ ID NO:4)
        SalI
5' GGG GGG GTC GAC CTC AGT TTT TAA CCC TTC 3'

M6 TS
                                         (SEQ ID NO:5)
        SalI
5' GGG GGG GTC GAC AGA GTG TTT CCT AGG GGG 3'

M6 BS
                                         (SEQ ID NO:6)
        NcoI
5' GGG GGG CCA TGG TAA CTT GTC ATT ATT AGC 3'

M19 TS
                                         (SEQ ID NO:7)
        NcoI
5' GGG GGG CCA TGG AGA GTG CGT TAT ACT AGG 3'

M19 BS
                                         (SEQ ID NO:8)
        PstI
5' GGG GGG CTG CAG AGA TAA CTT CTC ATT CTG 3'

M1 TS
                                         (SEQ ID NO:9)
        PstI
5' GGG GGG CTG GAG AAC GGT GAT GGT AAT CCT 3'

M1 BS
                                         (SEQ ID NO:10)
        KpnI
5' GGG GGG GGT ACC AGC TCT CTT AAA ATC TCT 3'

M3 TS
                                         (SEQ ID NO:11)
        KpnI
5' GGG GGG GGT ACC TTG TTA GAT GAG GTT ACA 3'

M3 BS
                                         (SEQ ID NO:12)
        ClaI
5' GGG GGG ATC GAT ATT TAA CTC TTG TAA CAG 3'

M24-2 TS
                                         (SEQ ID NO:13)
        ClaI
5' GGG GGG ATC GAT GTC GCG ACT AGG TCT CAG 3'

M24-2 BS
                                         (SEQ ID NO:14)
        HindIII
5' GGG GGG AAG CTT TTA CTT ACG TGC CTC TAA TTC 3'
```

PCR is performed on the chromosomal template as previously described (Dale et al., "Recombinant tetravalent group A streptococcal M protein vaccine," *J. Immunol.* 151:2188-2194, 1993). To assure ligation of the fragments in the correct orientation and reading frame, each PCR product is purified, ligated, and then subjected to PCR again using the forward primer from the 5' fragment and the reverse primer from the 3' fragment. For example, to construct a hexavalent emm gene containing DNA sequences from types 24, 5, 6, 19, 1, and 3 M proteins, the M24 and M5 gene fragments are amplified by PCR using the primers described above. The PCR products are purified from agarose gels, cut with the appropriate restriction enzyme, and ligated together (Dale et al., "Recombinant tetravalent group A streptococcal M protein vaccine," *J. Immunol.* 151:2188-2194, 1993; Dale et al., "Recombinant, octavalent group A streptococcal M protein vaccine," *Vaccine* 14:944-948, 1996). The ligation mixture is then amplified by PCR using the forward M24 primer and the reverse M5 primer. The resulting product of the appropriate size is then purified and ligated to the M6 and M19 gene fragment that was similarly constructed. After the final ligation reaction, the entire gene is amplified again by PCR, cut with the appropriate restriction enzymes and ligated into a suitable expression vector. For the addition of the reiterated M24 gene fragment in the 3' location, the plasmid was purified from the host *E. coli* and a new PCR product from emm 24 was force cloned into the 3' PstI restriction site.

The hexavalent gene was sequenced by the dideoxynucleotide chain termination method to confirm that each gene fragment was an exact copy of the respective native emm sequence.

Example 2

Purification of a Hexavalent Vaccine

A. Purification

Transformed *E. coli* were grown in a shaking incubator to log phase in 11 of LB containing 100 lag/ml ampicillin and 25 μg/ml kanamycin. IPTG (2 mM) was added for the final four hours of growth. The cell pellet was suspended in 30 ml PBS and lysed in a French pressure cell at 1000 psi. The hexavalent protein was purified from the supenatant using nickel nitrilotriacetic acid (Ni-NTA) resin according to the protocol provided by the manufacturer (Qiagen, Valencia, Calif.). The elution buffer containing the protein was concentrated from 15 ml to 5 ml in a spin filter (ULTRAFREE®-15, Millipore). Final purification was accomplished by gel filtration over SUPERDEX™ 75 (prep grade, Pharmacia Biotech). The active fraction was identified by Western blots (Dale, J. B. and Beachey, E. H., "Multiple heart-cross-reactive epitopes of streptococcal M proteins," *J. Exp. Med.* 161:113-122, 1985) using rabbit antiserum against pep M24 (Beachey et al., "Purification and properties of M protein extracted from group A *streptococci* with pepsin: Covalent structure of the amino terminal region of the type 24 M antigen," *J. Exp. Med* 145:1469-1483, 1977). Total protein concentration was determined by standard methods and the sample was diluted in PBS to contain 200 μg/ml of hexavalent protein. Purity of the samples was determined by gel scanning (PHOTOSHOP™ digital image and COLLAGE™ image analysis).

B. Analysis of the Hexavalent Vaccine

The structure of the hybrid emm gene was confirmed by double-stranded sequencing methods after ligation into pQE30. The sequence of each subunit was identical to the respective native emm gene (FIG. 1). The fragments were joined only by the two amino acids specified by each unique restriction site used to facilitate their ligation (FIG. 1).

Figure 2:
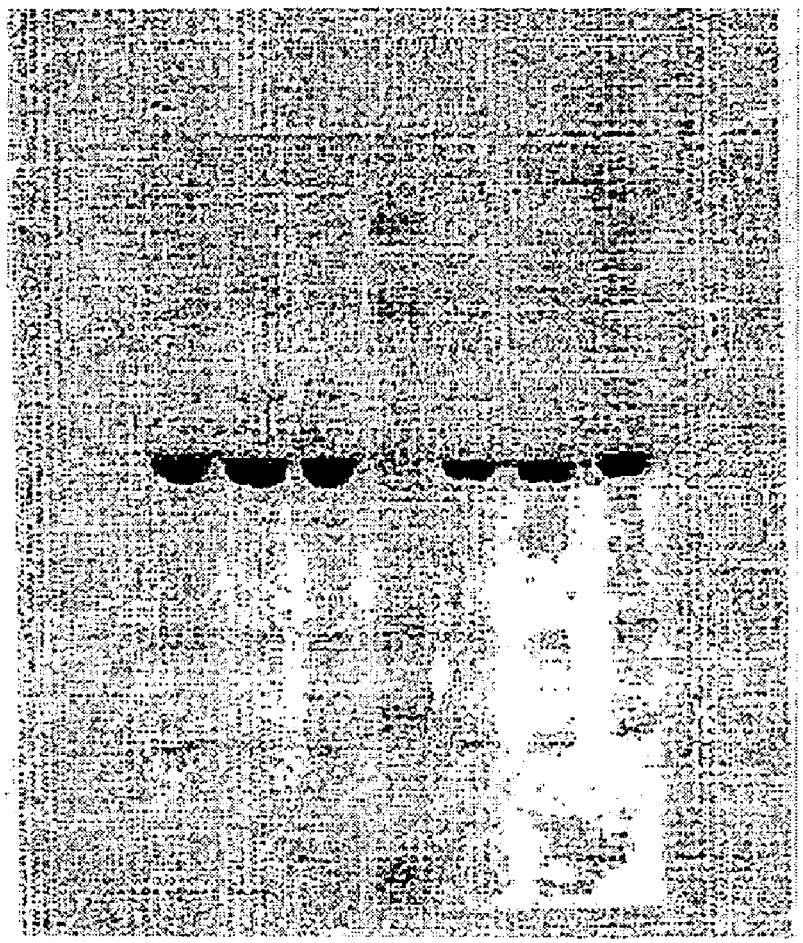

The purified hexavalent protein migrated on SDS-polyacrylamide gels with an apparent M. W. of 45 kDa. (FIG. 2). Gel scan analysis revealed that the intact hexavalent protein accounted for approximately 90% of the total stainable protein in the gel. Western blots using antisera against pep M24 showed that the majority of the remaining protein bands were immunoreactive and most likely were fragments of the hexavalent protein (data not shown).

Example 3

Immunization of Rabbits, and Testing of Antisera

A. Immunization

Two groups of three rabbits each were immunized with 100 µg of hexavalent vaccine either precipitated with alum or emulsified in complete Freund's adjuvant. For precipitation in alum, the hexavalent protein (200 µg/ml) was added to an equal volume of aluminum hydroxide (2 mg/ml) (REHYDRAGEL™ HPA, Reheis, Inc., Berkeley Heights, N.J.) and mixed gently at 4° C. overnight. The hexavalent protein was also emulsified in CFA at a final concentration of 100 µg/ml. Rabbits that received the hexavalent vaccine in alum were given 100 µg/ml as an initial injection and the same dose was repeated at 4, and 8 weeks. The second set of rabbits received 100 µg of hexavalent vaccine in CFA subcutaneously as an initial injection and then booster injections of the same dose in saline were given at 4 and 8 weeks. Blood was obtained prior to the first injection and at 2-week intervals thereafter.

Antibody assays. ELISAs were performed using purified native pepsin-extracted M proteins (Beachey et al., "Purification and properties of M protein extracted from group A *streptococci* with pepsin: Covalent structure of the amino terminal region of the type 24 M antigen," *J. Exp. Med.* 145:1469-1483, 1977) or the purified hexavalent protein, as previously described (Dale et al., "Heterogeneity of type-specific and cross-reactive antigenic determinants within a single M protein of group A *streptococci,*" *J. Exp. Med* 151:1026-1038, 1980). Opsonic antibodies were detected by in vitro opsonization assays and indirect bactericidal assays (Beachey et al., "Human immune response to immunization with a structurally defined polypeptide fragment of streptococcal M protein," *J. Exp. Med.* 150:862-877, 1979).

B. Detection of m Protein Antibodies.

The preimmune and immune animal sera are assayed by ELISA using the vaccine protein and the native pepsin-extracted M proteins as solid-phase antigens (Dale et al., "Heterogeneity of type-specific and cross-reactive antigenic determinants within a single M protein of group A *streptococci,*" *J. Exp. Med* 151:1026-1038, 1980). ELISA titers are defined as the inverse of the last dilution of antisera resulting in an OD of >0.1 at 450 nm. The titers of immune sera against the native M antigen are most likely to predict the levels of antibodies that are evoked by the recombinant protein that will react with the M protein on the surface of the respective serotype of *streptococcus* (i.e. promote opsonization).

C. Detection of Opsonic Antibodies.

Opsonic M protein antibodies correlate with protection against infection with the same serotype of group A *streptococci* (Lancefield, R. C., "Current knowledge of the type specific M antigens of group A *streptococci,*" *J. Immunol.* 89:307-313, 1962; Lancefield, R. C., "Persistence of type-specific antibodies in man following infection with group A *streptococci,*" *J. Exp. Med.* 110:271-282, 1959). Two related in vitro assays are used to detect opsonic antibodies in immune sera. The first is a screening assay that measures opsonization in mixtures of immune serum, whole, nonimmune human blood and the test organism (Beachey et al., "Purification and properties of M protein extracted from group A *streptococci* with pepsin: Covalent structure of the amino terminal region of the type 24 M antigen," *J. Exp. Med.* 145:1469-1483, 1977). 0.1 ml of test serum is added to a standard number of bacteria and incubated for 15 minutes at room temperature. 0.4 ml of lightly heparinized human blood is added and the entire mixture is rotated end-over-end at 37° C. for 45 minutes. At the end of the rotation, smears are prepared on microscope slides that are air-dried and stained with Wright's stain. "Percent opsonization" is quantitated by counting the percentage of polymorphonuclear leukocytes that have ingested or are associated with bacteria. An interpretable assay must have a preimmune control value that is 10% opsonization or less.

Confirmation of the presence of opsonic antibodies is obtained by indirect bactericidal antibody assays according to the original description by Lancefield (Lancefield, R. C., "Current knowledge of the type specific M antigens of group A *streptococci,*" *J. Immunol.* 89:307-313, 1962). This assay is performed using test mixtures as described above except that fewer bacteria are added and the rotation is allowed to proceed for 3 hours. At the end of the rotation, pour plates are made in sheep blood agar and bacteria surviving are quantitated after overnight growth at 37° C. Percent killing in the presence of immune serum is calculated by comparing to the growth in nonimmune serum.

Example 4

Mouse Protection Assays

A. General Protocol

Protective efficacy of M protein vaccines is determined by either indirect or direct (passive or active immunization) mouse protection tests. Indirect tests are performed by giving mice 1 ml of immune or preimmune serum via the intraperitoneal (i.p.) route 24 hours prior to challenge infections with the test organism given i.p. (Beachey et al., "Human immune response to immunization with a structurally defined polypeptide fragment of streptococcal M protein," *J. Exp. Med* 150:862-877, 1979). For each test organism, groups of 25 mice receive either preimmune or immune serum. The animals are then divided into 5 groups of 5 mice each and 10-fold increasing challenge doses of virulent *streptococci* are given to each subgroup. After 7 days of observation, the 50% lethal dose ($LD_{50}$) is calculated for each serotype tested.

Direct mouse protection tests are similarly performed except that mice are actively immunized with M protein vaccine prior to the challenge infections. Each mouse receives 25-50 ug vaccine in alum given intramuscularly (i.m.) at time 0, 4 weeks, and 8 weeks. Challenge infections are performed ten weeks after the first injection. Control animals are sham immunized with alum alone. The LD50 is calculated and significance is determined using Fisher's exact test.

B. Protection

In order to show directly the protective efficacy of opsonic antibodies evoked by the hexavalent vaccine, mice were immunized with the vaccine adsorbed to ALUM and then challenged with two of the serotypes represented in the vaccine. Female outbred white Swiss mice were immunized via the i.m. route in the hind leg according to the following schedule: time 0, 25 µg; 3 weeks, 25 µg; 6 weeks, 50 µg; and 13 weeks, 50 µg. Challenge experiments were performed on the 20 immunized mice and 20 control, unimmunized mice (Table 1). The challenge strains were types 24 and 19, with the reasoning that the M24 peptide is the largest fragment in the hexavalent protein and is reiterated and the M19 fragment is one of two that are only 35 amino acids long. These two fragments should reflect the range of protective immunogenicity of the hexavalent protein. Intraperitoneal challenge of mice with virulent streptococci is the most stringent laboratory assay for opsonic antibodies.

In this experiment, two groups of ten mice each were challenged with an inoculum that approximated the $LD_{70}$-$LD_{100}$ for each serotype, which was $2 \times 10^4$ CFU. The challenge experiments were begun 15 weeks after the first dose of vaccine was administered and deaths were recorded for 10 days. The mice that were immunized with the hexavalent vaccine and challenged with type 24 streptococci were significantly protected from death compared to the control group (p=0.0001). The mice challenged with type 19 streptococci were protected by vaccination, but the level was not statistically significant (p=0.15). Had the challenged group been twice the size, the same level of protection would have resulted in a statistically significant survival rate. When the survival of the entire immunized group of mice is analyzed, the level of protection was highly significant (p=0.0002).

TABLE 1

Protective immunogenicity of the hexavalent vaccine in mice that were challenged i.p. with virulent type 24 and type 19 streptococci

| Group | #Dead/#Survived of Mice Challenged (% survival) | | |
|---|---|---|---|
| | Type 24 | Type 19 | Total |
| Immunized mice | 0/10 (100) | 4/6 (60) | 4/16 (80) p = .0002* |
| Control mice | 9/1 (10) | 7/3 (30) | 16/4 (20) |

*p value was calculated using the Fisher exact test.

Example 5

Assays for Tissue-crossreactive Antibodies

To assure that none of the M protein vaccines evokes tissue-crossreactive antibodies, indirect immunofluorescence assays are performed using frozen sections of human heart, kidney, and brain (Dale, J. B. and Beachey E. H., "Protective antigenic determinant of streptococcal M protein shared with sarcolemmal membrane protein of human heart," J. Exp. Med. 156:1165-1176, 1982). Thin sections of tissue obtained at autopsy (4 um) are prepared on microscope slides and stored in a sealed box at −70° C. until use. Test serum is diluted 1:5 in PBS and dropped onto the tissue section. Control slides are made with preimmune serum and PBS. The slides are incubated at ambient temperature for 30 minutes and then washed three times in PBS in a slide holder. Fluorescein-labeled goat anti-IgG/IgM/IgA is diluted 1:40 in PBS and dropped onto the slides which are again washed, dried, and mounted with 1% GELVETOL and a coverslip. Fluorescence is detected using a Zeiss Axiophot microscope equipped with a xenon light source. Immunofluorescence is recorded using a scale of 0-4+, with 0 being no fluorescence and 4+ being that obtained with a standard, positive antiserum raised in rabbits against whole type 5 M protein (Dale, J. B. and Beachey, E. H., "Multiple heart-cross-reactive epitopes of streptococcal M proteins," J. Exp. Med. 161:113-122, 1985).

Example 6

Figure 3A:
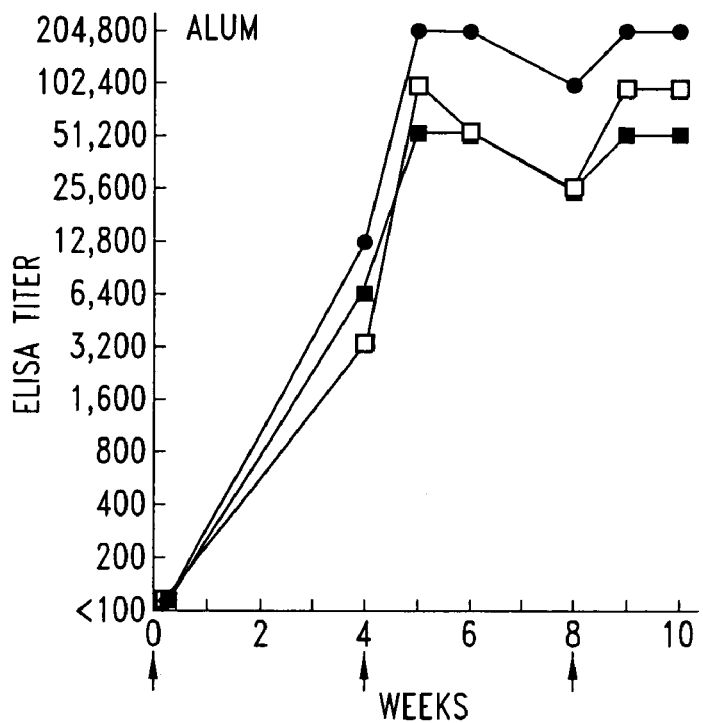
Figure 3B:
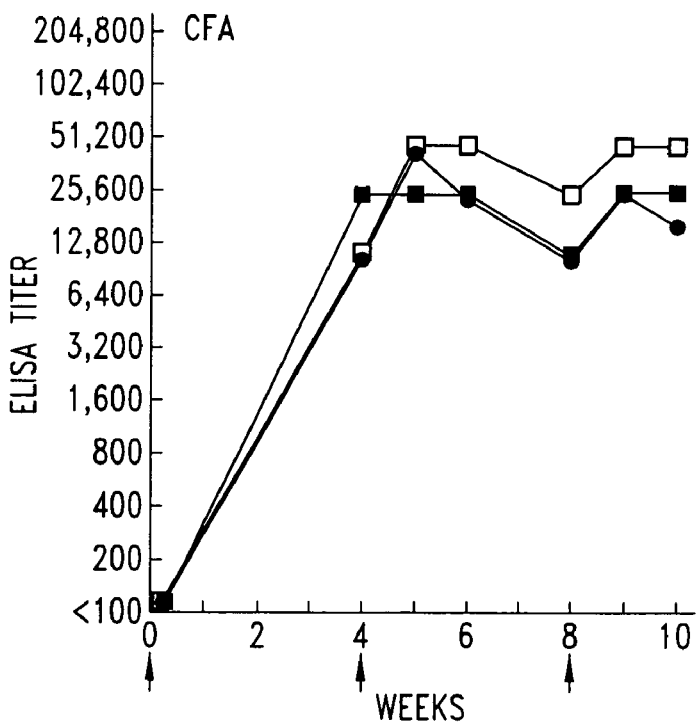
Figure 4A:
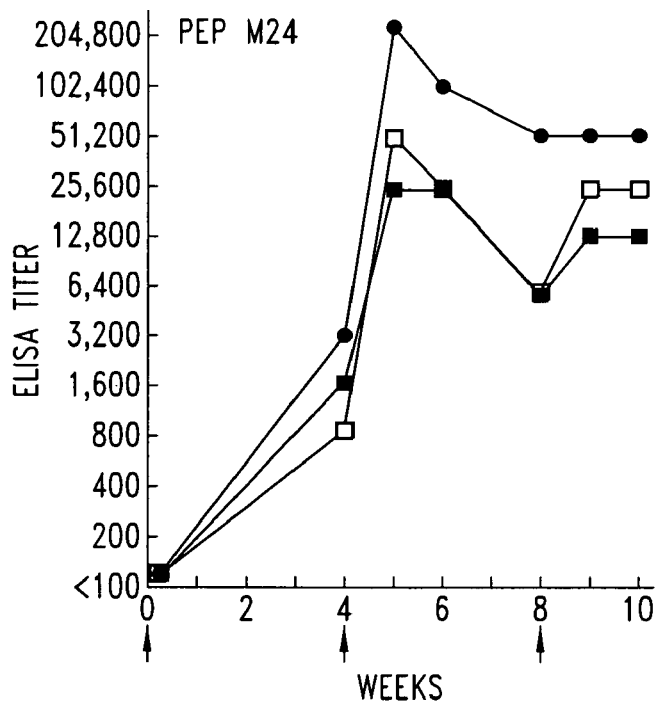
Figure 4B:
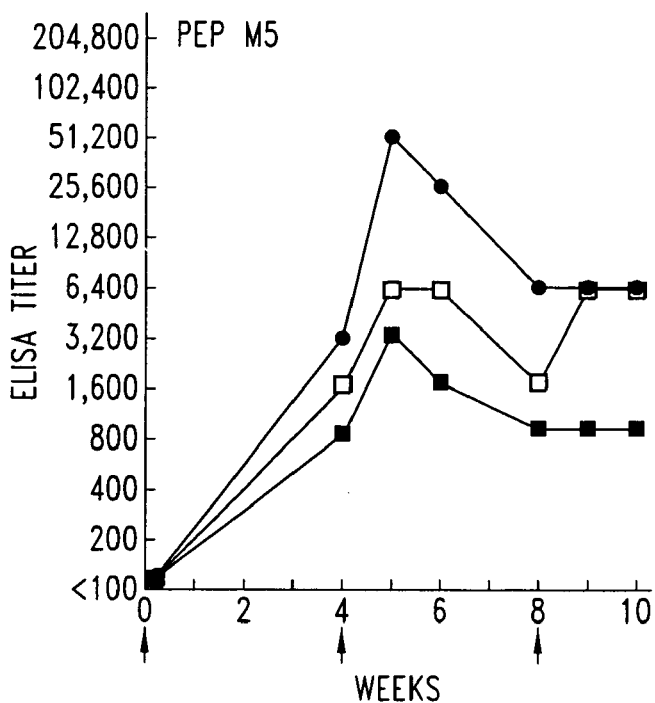
Figure 4C:
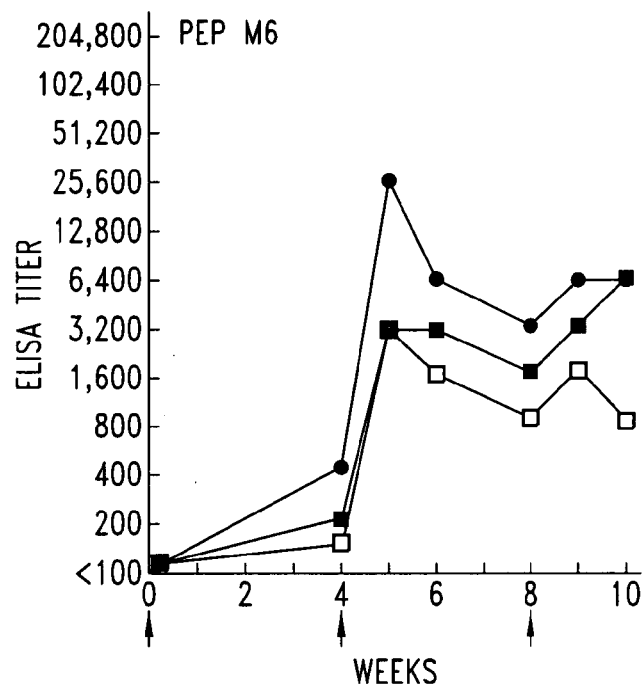
Figure 4D:
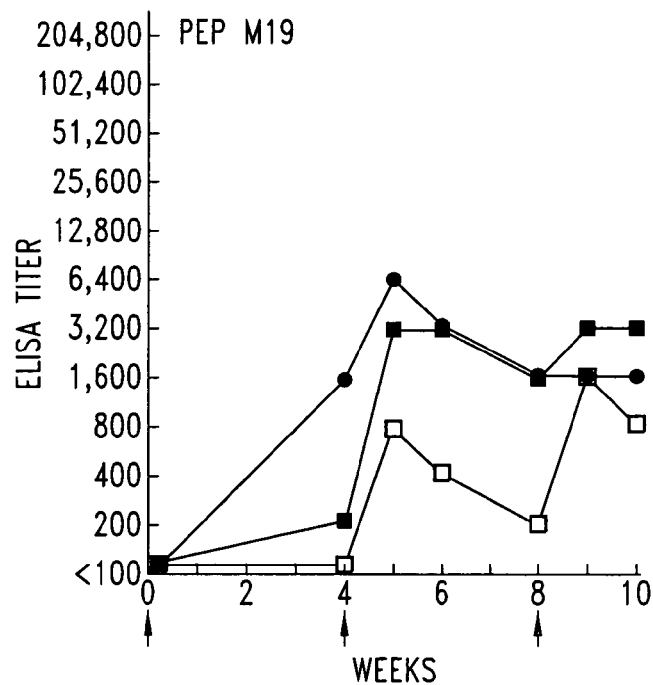
Figure 4E:
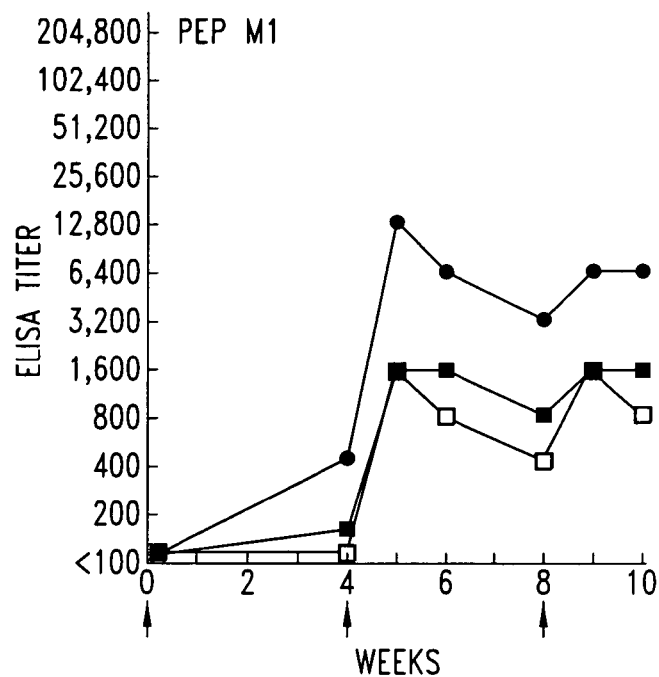
Figure 4F:
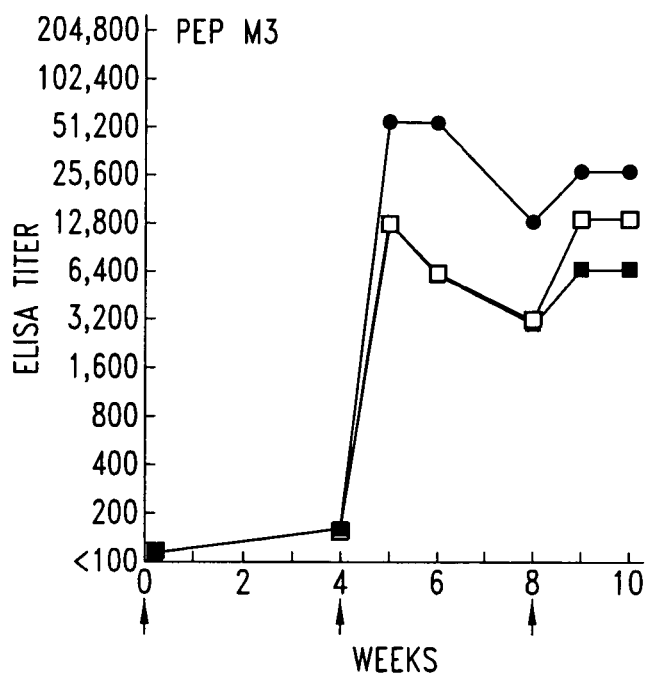

Comparison of the Immunogenicity of a Hexavalent Vaccine Delivered in Alum Versus Freund's Adjuvant Three rabbits each were immunized with 100 µg doses of the hexavalent vaccine in either alum or CFA. Booster injections of the same dose were given at 4 and 8 weeks in either alum or saline, respectively. ELISA titers were determined using the purified hexavalent protein as the solid phase antigen (FIG. 3). Sera from the animals that received the hexavalent vaccine in alum had antibody titers that were equal to or greater than the sera from rabbits that received the same dose in CFA. In a subsequent experiment, three rabbits were immunized i.m. with 100 µg of the hexavalent vaccine in saline alone according to the same schedule. None of these rabbits developed significant antibody titers against either the immunogen or the respective pep M proteins (data not shown). These data indicate that alum is a suitable and necessary adjuvant for the multivalent vaccine and is equal to the adjuvant activity of CFA in combination with the hexavalent protein.

Example 7

Protective Immunogenicity of the Component Subunits of a Hexavalent Vaccine

One of the major goals of this study was to design a multivalent, hybrid protein that retained the immunogenic properties of each M protein subunit. ELISAs were performed on sera obtained from the three rabbits immunized with the hexavalent vaccine in alum (FIG. 4). In each case the ELISA antigen was the purified pepsin-extracted M protein. Thus, the assay measures only the antibodies evoked by the hexavalent protein that react with the native M protein and not the antibodies that may be specific for the joining segments or conformations that are not present in the native M proteins. The hexavalent protein evoked significant levels of antibodies against each M protein represented in the vaccine construct (FIG. 4). Importantly, none of the antisera contained antibodies that crossreacted with human heart tissue or kidney tissue, as determined by indirect immunofluorescence assays (data not shown).

Figure 5:
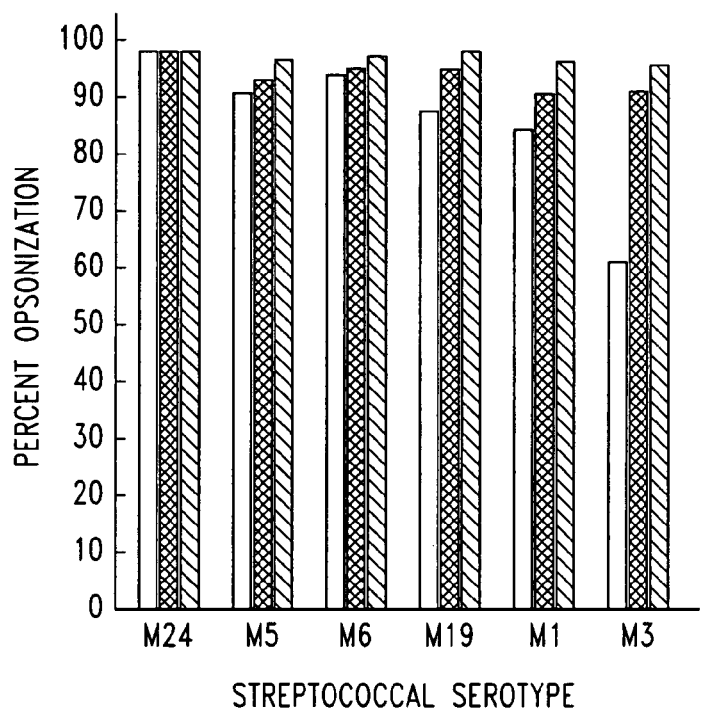

Sera from all three rabbits contained significant levels of opsonic antibodies against each serotype of group A streptococci represented in the vaccine (FIG. 5). These results were confirmed by indirect bactericidal assays using one of the immune sera (Table 2). Taken together, the results indicate that the individual components of the hexavalent vaccine retain the conformation and immunogenicity necessary to elicit antibodies that react with the native M proteins on the surface of each respective serotype of group A streptococci.

TABLE 2

Indirect bactericidal assay of rabbit antiserum against the hexavalent M protein vaccine.

| Serotype | Inoculum(CFU) | CFU Surviving 3 hr rotation: Preimmune | CFU Surviving 3 hr rotation: Immune | Percent Reduction |
|---|---|---|---|---|
| 24 | 12 | 2890 | 0 | 100 |
| 5 | 11 | 3260 | 0 | 100 |
| 6 | 6 | 2640 | 0 | 100 |
| 19 | 6 | 1580 | 0 | 100 |
| 1 | 8 | 2670 | 490 | 82 |
| 3 | 11 | 1720 | 10 | 99 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

SEQUENCE LISTING

<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Product of
      Synthesis -- Primer,  hybridizes to streptococcal
      type 24 M protein DNA

<400> SEQUENCE: 1
gggggggcat cggtcgcgac taggtctcag acagat                              36

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer,  hybridizes to streptococcal
      type 24 M protein DNA

<400> SEQUENCE: 2
ggggggggat ccacgtagtt tctctttagc                                     30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 5 M protein DNA

<400> SEQUENCE: 3
ggggggggat ccgccgtgac taggggtaca                                     30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 5 M protein DNA

```
<400> SEQUENCE: 4
gggggggtcg acctcagttt ttaacccttc                                      30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 6 M protein DNA

<400> SEQUENCE: 5 ggggggtcg acagagtgtt tcctagggg                                        30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 6 M protein DNA

<400> SEQUENCE: 6
ggggggccat ggtaacttgt cattattagc                                      30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 19 M protein DNA

<400> SEQUENCE: 7
ggggggccat ggagagtgcg ttatactagg                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 19 M protein DNA

<400> SEQUENCE: 8
ggggggctgc agagataact tctcattctg                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 1 M protein DNA

<400> SEQUENCE: 9
ggggggctgc agaacggtga tggtaatcct                                      30

<210> SEQ ID NO 10
<211> LENGTH: 30
<212> TYPE: DNA
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 1 M protein DNA

<400> SEQUENCE: 10
ggggggggta ccagctctct taaaatctct                                      30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 3 M protein DNA

<400> SEQUENCE: 11
ggggggggta ccttgttaga tcaggttaca                                      30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to streptococcal
      type 3 M protein DNA

<400> SEQUENCE: 12 gggggatcg atatttaact cttgtaacag                                       30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to strepptococcal
      type 24 M protein DNA

<400> SEQUENCE: 13 gggggatcg atgtcgcgac taggtctcag                                       30

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Product of
      Synthesis -- Primer, hybridizes to strepptococcal
      type 24 M protein DNA

<400> SEQUENCE: 14 gggggaagc ttttacttac gtgcctctaa ttc                                   33

<210> SEQ ID NO 15
<211> LENGTH: 1158
<212> TYPE: DNA
<213> ORGANISM: Artificial Sequence
<220> FEATURE:
<223> OTHER INFORMATION: Description of Artificial Sequence: Hexavalent
      M fusion gene sequence constructed from
      streptococcal type 24, 5, 6, 19, 1 and 3 M protein
      DNAs
<220> FEATURE:
<221> NAME/KEY: CDS
<222> LOCATION: (1)..(1149)

<400> SEQUENCE: 15

```
gca tgc atg gtc gcg act agg tct cag aca gat act ctg gaa aaa gta      48
Ala Cys Met Val Ala Thr Arg Ser Gln Thr Asp Thr Leu Glu Lys Val
 1               5                  10                  15 caa gaa cgt gct gac aag ttt gag ata gaa aac aat acg tta aaa ctt      96
Gln Glu Arg Ala Asp Lys Phe Glu Ile Glu Asn Asn Thr Leu Lys Leu
             20                  25                  30 aag aat agt gac tta agt ttt aat aat aaa gcg tta aaa gat cat aat     144
Lys Asn Ser Asp Leu Ser Phe Asn Asn Lys Ala Leu Lys Asp His Asn
         35                  40                  45 gat gag tta act gaa gag ttg agt aat gct aaa gag aaa cta cgt gga     192
Asp Glu Leu Thr Glu Glu Leu Ser Asn Ala Lys Glu Lys Leu Arg Gly
 50                  55                  60 tcc gcc gtg act agg ggt aca ata aat gac ccg caa aga gca aaa gaa     240
Ser Ala Val Thr Arg Gly Thr Ile Asn Asp Pro Gln Arg Ala Lys Glu
 65                  70                  75                  80 gct ctt gac aag tat gag cta gaa aac cat gac tta aaa act aag aat     288
Ala Leu Asp Lys Tyr Glu Leu Glu Asn His Asp Leu Lys Thr Lys Asn
             85                  90                  95 gaa ggg tta aaa act gag aat gaa ggg tta aaa act gag aat gaa ggg     336
Glu Gly Leu Lys Thr Glu Asn Glu Gly Leu Lys Thr Glu Asn Glu Gly
            100                 105                 110 tta aaa act gag aat gaa ggg tta aaa act gag gtc gac aga gtg ttt     384
Leu Lys Thr Glu Asn Glu Gly Leu Lys Thr Glu Val Asp Arg Val Phe
            115                 120                 125 cct agg ggg acg gta gaa aac ccg gac aaa gca cga gaa ctt ctt aac     432
Pro Arg Gly Thr Val Glu Asn Pro Asp Lys Ala Arg Glu Leu Leu Asn
130                 135                 140 aag tat gac gta gag aac tct atg tta caa gct aat aat gac aag tta     480
Lys Tyr Asp Val Glu Asn Ser Met Leu Gln Ala Asn Asn Asp Lys Leu
145                 150                 155                 160 cca tgg aga gtg cgt tat act agg cat acg cca gaa gat aag cta aaa     528
Pro Trp Arg Val Arg Tyr Thr Arg His Thr Pro Glu Asp Lys Leu Lys
                165                 170                 175 aaa att att gac gat ctt gac gca aaa gaa cat gaa tta caa caa cag     576
Lys Ile Ile Asp Asp Leu Asp Ala Lys Glu His Glu Leu Gln Gln Gln
            180                 185                 190 aat gag aag tta tct ctg cag aac ggt gat ggt aat cct agg gaa gtt     624
Asn Glu Lys Leu Ser Leu Gln Asn Gly Asp Gly Asn Pro Arg Glu Val
        195                 200                 205 ata gaa gat ctt gca gca aac aat ccc gca ata caa aat ata cgt tta     672
Ile Glu Asp Leu Ala Ala Asn Asn Pro Ala Ile Gln Asn Ile Arg Leu
210                 215                 220 cgt cac gaa aac aag gac tta aaa gcg aga tta gag aat gca atg gaa     720
Arg His Glu Asn Lys Asp Leu Lys Ala Arg Leu Glu Asn Ala Met Glu
225                 230                 235                 240 gtt gca gga aga gat ttt aag aga gct ggt acc ttg tta gat cag gtt     768
Val Ala Gly Arg Asp Phe Lys Arg Ala Gly Thr Leu Leu Asp Gln Val
                245                 250                 255 aca caa tta tat act aaa cat aat agt aat tac caa caa tat aat gca     816
Thr Gln Leu Tyr Thr Lys His Asn Ser Asn Tyr Gln Gln Tyr Asn Ala
            260                 265                 270 caa gct ggc aga ctt gac ctg aga caa aag gct gaa tat cta aaa ggc     864
Gln Ala Gly Arg Leu Asp Leu Arg Gln Lys Ala Glu Tyr Leu Lys Gly
        275                 280                 285 ctt aat gat tgg gct gag agg ctg tta caa gag tta aat atc gat gtc     912
Leu Asn Asp Trp Ala Glu Arg Leu Leu Gln Glu Leu Asn Ile Asp Val
290                 295                 300
```

-continued

```
gcg act agg tct cag aca gat act ctg gaa aaa gta caa gaa cgt gct        960
Ala Thr Arg Ser Gln Thr Asp Thr Leu Glu Lys Val Gln Glu Arg Ala
305                 310                 315                 320 gac aag ttt gag ata gaa aac aat acg tta aaa ctt aag aat agt gac       1008
Asp Lys Phe Glu Ile Glu Asn Asn Thr Leu Lys Leu Lys Asn Ser Asp
                325                 330                 335 tta agt ttt aat aat aaa gcg tta aaa gat cat aat gat gag tta act      1056
Leu Ser Phe Asn Asn Lys Ala Leu Lys Asp His Asn Asp Glu Leu Thr
            340                 345                 350 gaa gag ttg agt aat gct aaa gag aaa cta cgt aaa aat gat aaa tca      1104
Glu Glu Leu Ser Asn Ala Lys Glu Lys Leu Arg Lys Asn Asp Lys Ser
        355                 360                 365 cta tct gaa aaa gct agt aaa att caa gaa tta gag gca cgt aag           1149
Leu Ser Glu Lys Ala Ser Lys Ile Gln Glu Leu Glu Ala Arg Lys
    370                 375                 380 taaaagctt                                                             1158
```

<210> SEQ ID NO 16
<211> LENGTH: 383
<212> TYPE: PRT
<213> ORGANISM: Artificial Sequence
<220> FEATURE:
<223> OTHER INFORMATION: Description of Artificial Sequence:  Hexavalent
      M fusion gene sequence constructed from
      streptococcal type 24, 5, 6, 19, 1 and 3 M protein
      DNAs

<400> SEQUENCE: 16

```
Ala Cys Met Val Ala Thr Arg Ser Gln Thr Asp Thr Leu Glu Lys Val
  1               5                  10                  15

Gln Glu Arg Ala Asp Lys Phe Glu Ile Glu Asn Asn Thr Leu Lys Leu
             20                  25                  30

Lys Asn Ser Asp Leu Ser Phe Asn Asn Lys Ala Leu Lys Asp His Asn
         35                  40                  45

Asp Glu Leu Thr Glu Glu Leu Ser Asn Ala Lys Glu Lys Leu Arg Gly
     50                  55                  60

Ser Ala Val Thr Arg Gly Thr Ile Asn Asp Pro Gln Arg Ala Lys Glu
 65                  70                  75                  80

Ala Leu Asp Lys Tyr Glu Leu Glu Asn His Asp Leu Lys Thr Lys Asn
                 85                  90                  95

Glu Gly Leu Lys Thr Glu Asn Glu Gly Leu Lys Thr Glu Asn Glu Gly
            100                 105                 110

Leu Lys Thr Glu Asn Glu Gly Leu Lys Thr Glu Val Asp Arg Val Phe
        115                 120                 125

Pro Arg Gly Thr Val Glu Asn Pro Asp Lys Ala Arg Glu Leu Leu Asn
    130                 135                 140

Lys Tyr Asp Val Glu Asn Ser Met Leu Gln Ala Asn Asn Asp Lys Leu
145                 150                 155                 160

Pro Trp Arg Val Arg Tyr Thr Arg His Thr Pro Glu Asp Lys Leu Lys
                165                 170                 175

Lys Ile Ile Asp Asp Leu Asp Ala Lys Glu His Glu Leu Gln Gln Gln
            180                 185                 190

Asn Glu Lys Leu Ser Leu Gln Asn Gly Asp Gly Asn Pro Arg Glu Val
        195                 200                 205

Ile Glu Asp Leu Ala Ala Asn Asn Pro Ala Ile Gln Asn Ile Arg Leu
    210                 215                 220

Arg His Glu Asn Lys Asp Leu Lys Ala Arg Leu Glu Asn Ala Met Glu
225                 230                 235                 240
```

```
Val Ala Gly Arg Asp Phe Lys Arg Ala Gly Thr Leu Leu Asp Gln Val
            245                 250                 255

Thr Gln Leu Tyr Thr Lys His Asn Ser Asn Tyr Gln Gln Tyr Asn Ala
            260                 265                 270

Gln Ala Gly Arg Leu Asp Leu Arg Gln Lys Ala Glu Tyr Leu Lys Gly
            275                 280                 285

Leu Asn Asp Trp Ala Glu Arg Leu Leu Gln Glu Leu Asn Ile Asp Val
            290                 295                 300

Ala Thr Arg Ser Gln Thr Asp Thr Leu Glu Lys Val Gln Glu Arg Ala
305                 310                 315                 320

Asp Lys Phe Glu Ile Glu Asn Asn Thr Leu Lys Leu Lys Asn Ser Asp
            325                 330                 335

Leu Ser Phe Asn Asn Lys Ala Leu Lys Asp His Asn Asp Glu Leu Thr
            340                 345                 350

Glu Glu Leu Ser Asn Ala Lys Glu Lys Leu Arg Lys Asn Asp Lys Ser
            355                 360                 365

Leu Ser Glu Lys Ala Ser Lys Ile Gln Glu Leu Glu Ala Arg Lys
370                 375                 380
```

I claim:

1. A method for eliciting an immune response against Group A *streptococci* comprising administering to a patient a pharmaceutical composition comprising (a) a recombinant fusion polypeptide wherein said recombinant fusion polypeptide comprises a multivalent immunogenic portion fused to an immunogenic polypeptide carboxy-terminal to the multivalent immunogenic portion, which protects the immunogenicity of the multivalent immunogenic portion, wherein the multivalent immunogenic portion comprises at least two immunogenic amino-terminal polypeptides of Group A streptococcal M protein from at least two different Group A streptococcal serotypes, wherein the immunogenic polypeptide carboxy-terminal to the multivalent immunogenic portion is a reiteration of the immunogenic amino-terminal polypeptide from the amino terminus of the multivalent immunogenic portion, and wherein each of the at least two immunogenic amino-terminal polypeptides is at least 10 amino acids in length, and (b) a pharmaceutically acceptable excipient, carrier, stabilizer or diluent, thereby eliciting said immune response against said Group A *streptococci*.

2. The method according to claim 1 wherein at least one of said immunogenic amino-terminal polypeptides of the fusion polypeptide is from a Group A streptococcal serotype selected from the group consisting of 1, 2, 3, 4, 5, 6, 11, 12, 13, 14, 18, 19, 22, 24, 28, 30, 48, 49, 52, and 56.

3. The method according to claim 1 wherein the multivalent immunogenic portion of the fusion polypeptide consists of six immunogenic amino-terminal polypeptides of Group A streptococcal M protein from six different Group A streptococcal serotypes.

4. The method according to claim 3 wherein the six different Group A streptococcal serotypes are 1, 3, 5, 6, 19, and 24.

5. The method according to claim 1 wherein the multivalent immunogenic portion of the fusion polypeptide consists of ten different Group A streptococcal serotypes.

6. The method according to claim 5 wherein the ten different Group A streptococcal serotypes are 1, 3, 5, 6, 18, 19, 22, 24, 28, and 30.

7. The method according to any one of claims 1 to 3 wherein at least one of the immunogenic amino-terminal polypeptides of the fusion polypeptide is from a Group A streptococcal serotype 1.

8. The method according to any one of claims 1 to 3 wherein at least one of the immunogenic amino-terminal polypeptides of the fusion polypeptide is from a Group A streptococcal serotype 2.

9. The method according to any one of claims 1 to 3 wherein at least one of the immunogenic amino-terminal polypeptides of the fusion polypeptide is from a Group A streptococcal serotype 11.

10. The method according to any one of claims 1 to 3 wherein at least one of the immunogenic amino-terminal polypeptides of the fusion polypeptide is from a Group A streptococcal serotype 24.

11. The method according to any one of claims 1 to 3 wherein at least one of the immunogenic amino-terminal polypeptides of the fusion polypeptide is from a Group A streptococcal serotype 19.

12. The method according to any one of claims 1 to 3 wherein at least one of the immunogenic amino-terminal polypeptides of the fusion polypeptide is from a Group A streptococcal serotype 22.

13. The method according to any one of claims 1 to 3 wherein at least one of the immunogenic amino-terminal polypeptides of the fusion polypeptide is from a Group A streptococcal serotype 28.

14. The method according to any one of claims 1 to 3 wherein the administered composition elicits an immune response comprising opsonic antibodies against Group A streptococcal M protein that do not cross-react with human tissue.

15. The method according to claim 1 wherein the recombinant fusion polypeptide further comprises a selectable marker encoded by an expression vector.

16. The method according to claim 15 wherein the expression vector is a 6× His-tag vector.

17. The method according to claim 16 wherein the selectable marker binds to nickel nitrilotriacetic acid (Ni-NTA) resin.

18. The method according to any one of claims 1 to 3 wherein the immunogenic polypeptides of the fusion polypeptide are joined by amino acids specified by a restriction enzyme site.

19. The method according to claim 1 wherein the patient is human.

20. The method according to claim 1 or claim 19 wherein the composition is administered via subcutaneous route, intramuscular route, or mucosal route.

21. The method according to claim 20 wherein the composition is administered via the intramuscular route to said patient at a concentration of 50 μg to 300 μg.

22. The method according to any one of claims 1 to 3 wherein the composition further comprises an adjuvant.

23. The method according to claim 22 wherein the adjuvant is alum.

24. The method according to claim 22 wherein the composition further comprises an immunomodulatory cofactor.

25. The method according to claim 1 or claim 22 wherein the composition comprises at least one of a buffer, antioxidant, carbohydrate, and chelating agent.

26. The method according to claim 24 wherein the immunomodulatory cofactor is selected from the group consisting of IL-4, IL-10, γ-IFN, IL-2, IL-12, and IL-15.

* * * * *

UNITED STATES PATENT AND TRADEMARK OFFICE
CERTIFICATE OF CORRECTION

PATENT NO. : 7,255,863 B2 Page 1 of 1
APPLICATION NO. : 10/759600
DATED : August 14, 2007
INVENTOR(S) : James B. Dale It is certified that error appears in the above-identified patent and that said Letters Patent is hereby corrected as shown below:

Title Page
Item (56), References Cited, Other Publications, should include the following references,
--QIAGEN News, Issue 4, 1-5, 1997--.
--QIAexpress®: The Complete System for 6xHis Technology, 1-31, 06/2000--.
--pQE-30, pQE-31, and pQE-32 Vectors, 1-A QIAGEN document--.

Signed and Sealed this

Fifth Day of August, 2008

JON W. DUDAS
*Director of the United States Patent and Trademark Office*